United States Patent [19]

Lodhi et al.

[11] 4,431,833

[45] Feb. 14, 1984

[54] PROSTAGLANDIN AND HYDROXYLATED FATTY ACID ESTER FORMULATIONS

[75] Inventors: Shahid A. Lodhi, Spring Valley; Bernard Sims, Monsey, both of N.Y.

[73] Assignee: American Cyanamid Company, Stamford, Conn.

[21] Appl. No.: 453,633

[22] Filed: Dec. 27, 1982

[51] Int. Cl.$^3$ .................. C07C 177/00; A61K 31/557
[52] U.S. Cl. ........................................ 560/2; 562/503; 568/379; 474/305; 474/317; 474/331
[58] Field of Search ......................... 560/2; 562/503; 568/379; 424/305, 317, 331

[56] References Cited

U.S. PATENT DOCUMENTS

| | | | |
|---|---|---|---|
| 3,296,091 | 1/1967 | Beal | 195/30 |
| 3,966,962 | 6/1976 | Yalkowsky | 424/305 |
| 4,178,454 | 12/1979 | Naruto | 560/2 |
| 4,242,366 | 12/1980 | Morgan | 426/554 |
| 4,310,543 | 1/1982 | Gallo-Torres | 424/305 |

*Primary Examiner*—Robert Gerstl
*Attorney, Agent, or Firm*—Mary-Ellen M. Timbers

[57] ABSTRACT

Degradation of E-type prostaglandin compounds is retarded by dissolving or suspending such compounds in formulations containing hydroxylated derivatives of fatty acids having the formula:

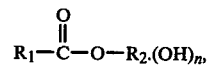

wherein $R_1$ is $C_2$–$C_{24}$ alkyl, $R_2$ is $C_2$–$C_{24}$ alkyl and n is an integer from 1–6, denoting from 1 to 6 hydroxyl groups which may be substituted in $R_1$ or $R_2$.

10 Claims, No Drawings

PROSTAGLANDIN AND HYDROXYLATED FATTY ACID ESTER FORMULATIONS

BACKGROUND OF THE INVENTION

Prostaglandins are a group of cyclic fatty acids that possess diverse and potent biologic activities affecting cell function in every organ system. The parent compound, prostanoic acid, contains a 20 carbon chain with a cyclopentane ring.

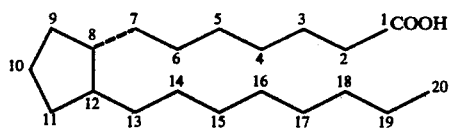

PROSTANOIC ACID

Variations in the number and position of the double bonds and hydroxyl groups determine the physiologic activities of the various prostaglandins.

Conventionally, prostaglandins are divided into types E, F, A, B, C and D based on functions in the cyclopentane ring. Numerical subscripts refer to the number of unsaturations in the side chains. $\alpha$ or $\beta$ subscripts refer to the configuration of the substituents in the ring. The naturally occurring prostaglandins are types E, F, A and B. All naturally occurring prostaglandins have a trans=13,14 position bond and a hydroxyl group at $C_{15}$.

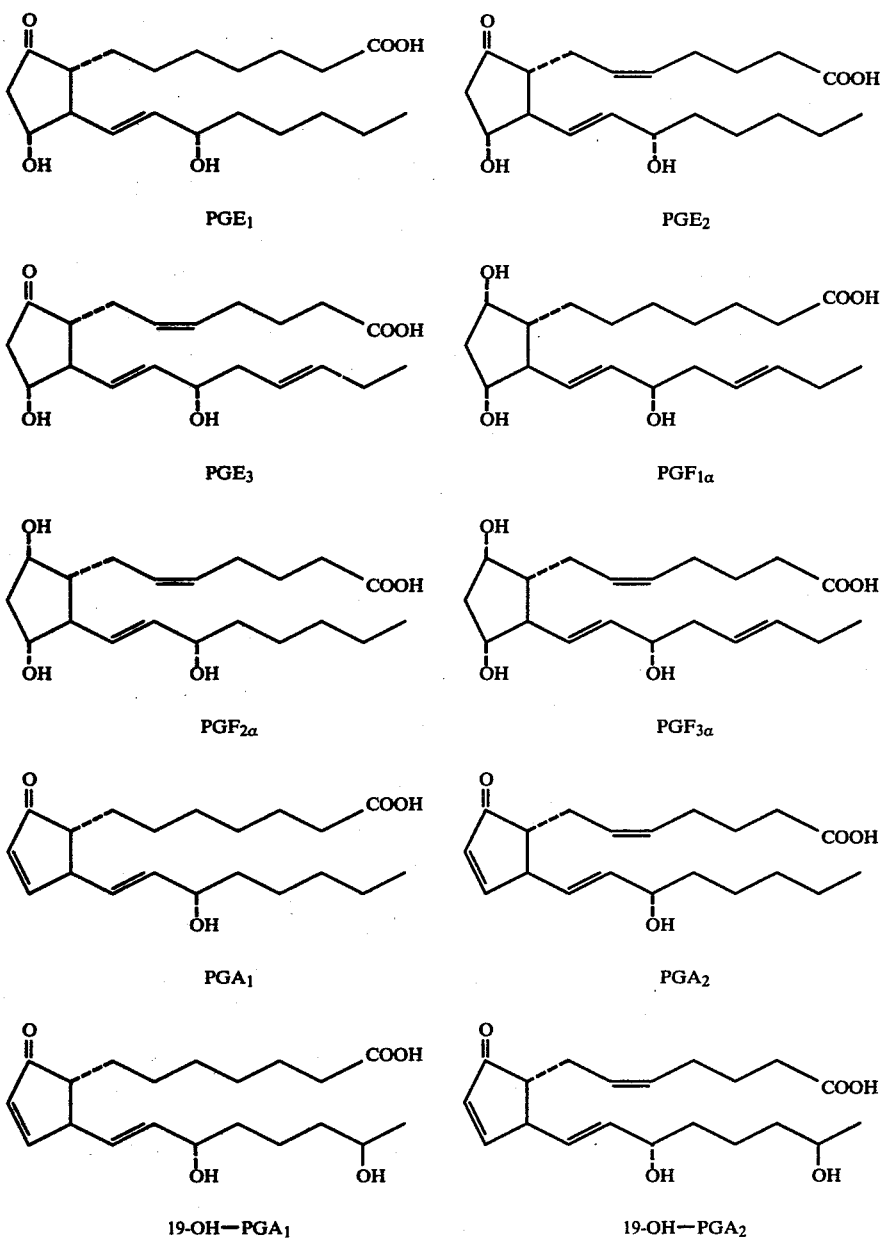

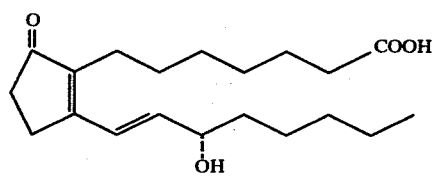

PGB₁

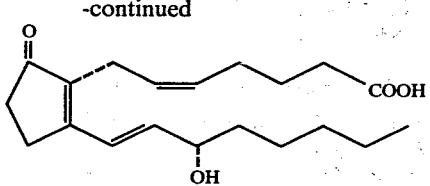

-continued

PGB₂

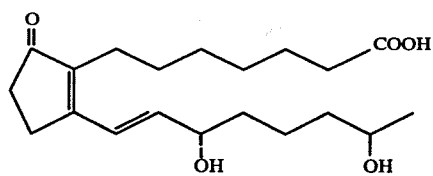

19-OH—PGB₁

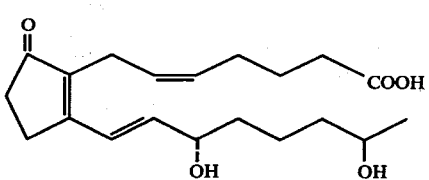

19-OH—PGB₂

Further, the E- and F-types possess an additional hydroxyl at $C_{11}$. At $C_9$, E-type prostaglandins have a carbonyl function while F-type prostaglandins have a hydroxyl. In general, A- and B-type prostaglandins may be regarded as dehydration products of E- and F-type prostaglandins; i.e., the removal of the $C_{11}$ hydroxyl and the formation of a double bond in the cyclopentane ring.

The biologic activities of prostaglandins of the E-type include activities as hypotensive agents, antilipodemic agents, bronchodilators, fertility control agents and gastric secretion inhibition agents. Bergstrom, et al., PHARMACOL., REV., 20:1 (1968); see also U.S. Pat. No. 3,069,322 and U.S. Pat. No. 3,598,858. However, E-type prostaglandins generally decompose at room temperature and above, and also in the presence of small amounts of acid or base. Accordingly, E-type prostaglandins are unstable in conventional pharmaceutical formulations. Even in neutral aqueous solution or in a neat state there is a gradual decomposition of E-type prostaglandins to A- and B-type prostaglandins. Stability of the E-type prostaglandins has been observed in some solutions and in solid form at −20° C. or lower. However, storage at such temperatures is impractical and administration to mammals at such temperatures is practically impossible. Some success at stabilization has been reported in: U.S. Pat. No. 3,749,800; U.S. Pat. No. 3,826,823; U.S. Pat. No. 3,829,579; and U.S. Pat. No. 3,851,052; see also Srivastava et al., LIPIDS, 8:592 (1973); where ethyl acetate, chloroform and ethanol are employed as solvents for E-type prostaglandins. Such solvents, however, are unsuitable for pharmaceutical dosage applications without dilution with water, which causes rapid decomposition.

More recently, stability of E-type prostaglandins was reported with use of triethyl citrate as a solvent, U.S. Pat. No. 4,211,793.

SUMMARY OF THE INVENTION

E-type prostaglandins dissolved, suspended or emulsified in hydroxylated derivatives of fatty acids are stable and in a form suitable for pharmaceutical use; i.e., direct administration to warm-blooded animals. Prostaglandins stabilized by the method of this invention are particularly adaptable for topical administration.

In particular, the following E-type prostaglandins, having vasodilator and hypotensive activities, remain stable in hydroxylated derivatives of fatty acids:

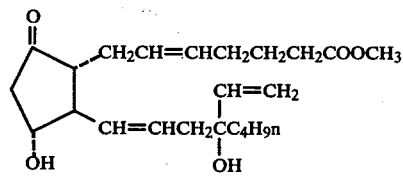

7-[2β-(4-butyl-4-hydroxy-1,5-hexadienyl-3α-hydroxy-5-oxo-1α-cyclopentyl]-5-heptenoic acid, methyl ester

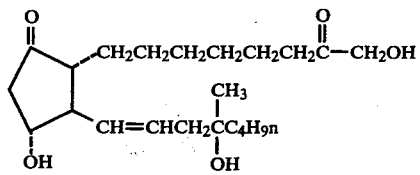

1-hydroxy-8-[3α-hydroxy-2β-(4-hydroxy-4-methyl-1-octenyl)-5oxo-1α-cyclopentyl]-2-octanone.

Hydroxylated derivatives of fatty acids useful in the present invention are presented by the formula

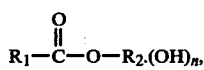

where $R_1$ is a straight or branched chain alkyl group ($C_2$–$C_{24}$); $R_2$ is a straight or branched chain alkyl group ($C_2$–$C_{24}$); and n is an integer from 1 to 6, denoting from 1 to 6 hydroxyl groups which may be substituted in alkyl groups $R_1$ or $R_2$. The preferred derivative is 2-ethylhexyl-12-hydroxystearate

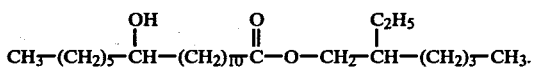

Pharmaceutical preparations of E-type prostaglandins suitable for topical application may be prepared by dissolving, suspending or emulsifying such prostaglandins in hydroxylated stearic acid derivatives of the above formula. Depending upon the physical state of the derivative at room temperature, a solution, suspension or ointment is produced. The state of the formulation may be altered, if desired, by the addition of solvents such as mineral oil, isopropyl myristate or similar fatty acid esters. For example, E-type prostaglandin may be dissolved in an hydroxylated derivative of a fatty acid at a concentration of about 0.0001 to about 200 mg per ml forming, depending upon the derivative selected, a clear solution or suspension. Preferably, an E-type prostaglandin is dissolved in 2-ethylhexyl-12-hydroxystearate at a concentration of about 0.0001 to about 200 mg per ml, forming a clear solution.

The stability of E-type prostaglandins in hydroxylated derivatives of fatty acids formulations has been demonstrated in an accelerated stability study comparing 1-hydroxy-8-[3α-hydroxy-2β-(4-hydroxy-4-methyl-1-octenyl)-5-oxo-1α-cyclopentyl]-2-octanone at a concentration of about 1% in three different solutions as follows:

Solution A—2-ethylhexyl-12-hydroxystearate
Solution B—2-ethylhexyl stearate
Solution C—triethyl citrate The study was conducted at about 100° C. over a period of about 148 hours. The results appear in Table I.

TABLE I

| Time | % Degradation | | |
|---|---|---|---|
| (Hours) | Solution A | Solution B | Solution C |
| 0 | 0 | 0 | 0 |
| 3.5 | 2.2 | 10.6 | 9.1 |
| 19 | 9.9 | 26.6 | 11.2 |
| 27 | 15.6 | — | — |
| 52 | 36.4 | 35.3 | 43.3 |
| 148 | 56.7 | 85.0 | 16.1 |

The above results show that solution A retains almost half its activity after 148 hours as opposed to solution B, employing the non-hydroxylated stearic acid analog and solution C, employing triethyl citrate, both of which show almost complete degradation.

The following examples were conducted at room temperature (about 15° C. to about 20° C.) and at atmospheric pressure.

EXAMPLE 1

To about 9.90 g of 2-ethylhexyl 12-hydroxystearate was added about 0.1 g of 1-hydroxy-8-[3α-hydroxy-2β-(4-hydroxy-4-methyl-1-octenyl)-5-oxo-1α-cyclopentyl]-2-octanone. The mixture was stirred with a lightning mixer for about 15 minutes to dissolve the prostaglandin and produce a solution.

EXAMPLE 2

The process of Example 1 was repeated substituting about 0.1 g of 7-[2β-(4-butyl-4-hydroxy-1,5-hexadienyl)-3α-hydroxy-5-oxo-1α-cyclopentyl]-5-heptenoic acid, methyl ester, producing a solution.

EXAMPLE 3

The process of Example 1 was repeated substituting about 0.1 g of PGE$_2$, producing a solution.

EXAMPLE 4

| Formula: | |
|---|---|
| 2-Ethylhexyl 12-hydroxystearate | about 9.9 g |
| 7-[2β-(4-Butyl-4-hydroxy-1,5-hexadienyl)-3α-hydroxy-5-oxo-1α-cyclopentyl]-5-heptanoic acid, methyl ester | about 0.5 g |
| Parafin wax | about 8.0 g |
| Petrolatum qs | about 100 g |

The petrolatum and parafin wax are melted at about 65° C. in one container. In a separate container the prostaglandin is dissolved in the 2-ethylhexyl 12-hydroxystearate using a lightning mixer for about 15 minutes. The contents of both containers are combined and cooled to about 45° C. while stirring with a lightning mixer producing an ointment.

The above examples are merely illustrative of the invention and not limitations on the invention.

What is claimed is:

1. A method for stabilizing E-type prostaglandins comprising the step of admixing an E-type prostaglandin with an amount of hydroxylated derivative of a fatty acid having the formula

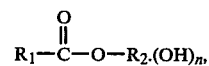

where R$_1$ is C$_2$–C$_{24}$ alkyl; R$_2$ is C$_2$–C$_{24}$ alkyl; and n is an integer from 1 to 6, denoting from 1 to 6 hydroxyl groups which may be substituted in the alkyl groups R$_1$ or R$_2$, effective to stabilize the prostaglandin.

2. The method as recited in claim 1, wherein the prostaglandin is 1-hydroxy-8-[3α-hydroxy-2β-(4-hydroxy-4-methyl-1-octenyl)-5-oxo-1α-cyclopentyl]-2-octanone.

3. The method as recited in claim 1, wherein the prostaglandin is 7-[2β-(4-butyl-4-hydroxy-1,5-hexadienyl)-3α-hydroxy-5-oxo-1α-cyclopentyl]-5-heptenoic acid, methyl ester.

4. The method as recited in claim 1, wherein the hydroxylated derivative of a fatty acid is 2-ethylhexyl-12-hydroxystearate.

5. The method as recited in claim 1, wherein about one milliliter of the hydroxylated derivative of a fatty acid is admixed with between about 0.0001 mg to about 200 mg of the prostaglandin.

6. A stable E-type prostaglandin formulation comprising an E-type prostaglandin, and an amount of hydroxylated derivative of a fatty acid represented by the formula

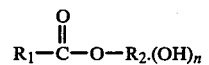

wherein R$_1$ is C$_2$–C$_{24}$ alkyl; R$_2$ is C$_2$–C$_{24}$ alkyl; and wherein n is an integer from 1 to 6, denoting from 1 to 6 hydroxyl groups which may be substituted in alkyl groups R$_1$ or R$_2$ effective to stabilize the prostaglandin.

7. The formulation as recited in claim 6 wherein prostaglandin is 1-hydroxy-8-[3α-hydroxy-2β-(4-hydroxy-4-methyl-1-octenyl)-5-oxo-1α-cyclopentyl]-2-octanone.

8. The formulation as recited in claim 6 wherein the prostaglandin is 7-[2β-(4-butyl-4-hydroxy-1,5-hexadienyl)-3α-hydroxy-5-oxo-1α-cyclopentyl]-5-heptenoic acid, methyl ester.

9. The formulation as recited in claim 6 wherein the hydroxylated derivative of a fatty acid is 2-ethylhexyl-12-hydroxystearate.

10. The formulation as recited in claim 6 wherein the amount of hydroxylated derivative of a fatty acid is about one milliliter per about 0.0001 mg to about 200 mg of the prostaglandin.

* * * * *